United States Patent [19]

Hofmann et al.

[11] Patent Number: 5,507,724
[45] Date of Patent: Apr. 16, 1996

[54] ELECTROPORATION AND IONTOPHORESIS APPARATUS AND METHOD FOR INSERTION OF DRUGS AND GENES INTO CELLS

[75] Inventors: Gunter A. Hofmann; Lois J. Crandell, both of San Diego, Calif.

[73] Assignee: Genetronics, Inc., San Diego, Calif.

[21] Appl. No.: 183,963

[22] Filed: Jan. 21, 1994

Related U.S. Application Data

[63] Continuation-in-part of Ser. No. 907,322, Jul. 1, 1992, Pat. No. 5,304,120.

[51] Int. Cl.⁶ .................................................. A61M 31/00
[52] U.S. Cl. ........................ 604/53; 604/21; 604/101; 607/116
[58] Field of Search .................... 604/20–22, 96, 604/113–114, 49, 52, 53; 607/115, 116, 122

[56] References Cited

U.S. PATENT DOCUMENTS

| | | | |
|---|---|---|---|
| 3,680,544 | 8/1972 | Shinnick et al. | 128/2 R |
| 4,709,698 | 12/1987 | Johnston et al. | 604/114 X |
| 5,002,527 | 3/1991 | Reller et al. | 604/20 |
| 5,042,975 | 8/1991 | Chien et al. | 604/20 |
| 5,098,843 | 3/1992 | Calvin | 435/287 |
| 5,117,828 | 6/1992 | Metzger et al. | 128/642 |
| 5,137,817 | 8/1992 | Busta et al. | 435/173 |
| 5,154,165 | 10/1992 | Elliott et al. | 128/419 |
| 5,236,413 | 8/1993 | Feiring | 604/21 |
| 5,256,141 | 10/1993 | Gencheff et al. | 604/53 |
| 5,279,046 | 1/1994 | Mische et al. | 604/22 |
| 5,282,785 | 2/1994 | Shapland et al. | 604/21 |
| 5,286,254 | 2/1994 | Shapland et al. | 604/21 |
| 5,423,744 | 6/1995 | Gencheff et al. | 604/53 |

FOREIGN PATENT DOCUMENTS

| | | |
|---|---|---|
| 0315982 | 11/1988 | Germany . |
| 1069826 | 9/1982 | U.S.S.R. . |
| WO91/16945 | 11/1991 | WIPO . |
| WO92/07605 | 5/1992 | WIPO . |

*Primary Examiner*—Corrine M. McDermott
*Attorney, Agent, or Firm*—Baker, Maxham, Jester & Meador

[57] ABSTRACT

A catheter device having a plurality of axially extending, circumferentially spaced electrodes carried thereby, infusion means for infusion of fluid medium for carrying genes and drugs, and expandable sealing means at each end of the electrodes for sealing off and confining the therapeutic medium to the area to be treated is inserted into a selected blood vessel of a patient and advanced to a preselected location within the blood vessel where cells on or near the wall of the vessel are to be treated. Once in place, the catheter device is expanded so that the plurality of axially extending, circumferentially spaced electrodes carried thereby are in contact with the inner wall of the blood vessel and seals at each end of the electrodes expand and seal the catheter device in the preselected location. A quantity of therapeutic genes or drugs is infused into the area of the electrodes via a tube and a conventional pump. A power pack connected to the electrodes is energized subjecting the cells to electric fields of predetermined amplitude and duration making the walls of the cells transiently permeable to enabling therapeutic genes or drugs carried by the fluid medium to enter the cells without killing them.

22 Claims, 2 Drawing Sheets

ELECTROPORATION AND IONTOPHORESIS APPARATUS AND METHOD FOR INSERTION OF DRUGS AND GENES INTO CELLS

REFERENCE TO RELATED APPLICATIONS

The present application is a continuation-in-part of my application Ser. No. 07/907,322, filed Jul. 1, 1992 entitled "ELECTROPORATION METHOD AND APPARATUS FOR INSERTION OF DRUGS AND GENES INTO ENDOTHELIAL CELLS" now U.S. Pat. No. 5,304,120.

BACKGROUND OF THE INVENTION

The present invention relates to the treatment of ailments in humans and other mammals, and more particularly, to a method and apparatus for delivering pharmaceutical compounds and genes into the endothelial and other nearby cells of a patient.

In the above identified prior application there is disclosed a catheter device which is inserted into a selected blood vessel of a patient and advanced to a preselected location within the blood vessel where the endothelial cells on the inner wall of the vessel are to be treated. Once in place, the catheter device is expanded so that a plurality of axially extending, circumferentially spaced electrodes carried thereby are in contact with the inner wall of the blood vessel. A fluid medium is then infused into the blood vessel adjacent the electrodes via infusion ports communicating by supply lines from a conventional pump. A power pack connected to the electrodes is energized to apply a predetermined voltage pulse to the electrodes and generate electric fields of predetermined amplitude. This subjects the endothelial cells to electric fields of predetermined amplitude and duration in making the walls of the endothelial cells transiently permeable to permit therapeutic genes or drugs carried by the fluid medium to enter the endothelial cells without killing them.

Endothelial cells are in direct contact with the blood stream and cover almost one thousand square meters of the inner surface of the blood vessels of a human. The blood vessels extend throughout the body and closely adjacent to almost all tissue of the body. The invention of the parent application was developed primarily to treat damage to endothelial cells which has been linked to cardiovascular diseases such as arteriosclerosis and high blood pressure. Endothelial cell damage may result from surgical procedures such as heart transplantation and by balloon angioplasty and routing of the blood vessels with rotary and laser catheters. These procedures are frequently used to remove blockage in the coronary arteries, however, the resulting trauma and scarring to the lumen walls can lead to rapid return of fatty deposits and a recurrence of blockage. Our studies have indicated that genetic modification of the endothelial cells might correct the damage caused by surgical procedures and could reduce the rate of deposit of low density cholesterol before and after surgical procedures. Insertion of drugs directly into the cells also appears to be effective to alleviate problems associated with damage to these cells.

The blood vessels can also be used to transport genes and drugs to areas for treatment of tissue and cells in areas adjacent to the vessels. They can also be used to place field generating means adjacent the areas to be treated. We have developed methods and apparatus for combined iontophoresis and electroporation for delivery of genes and drugs via the blood vessels into endothelial and other adjacent cells in the body. Electroporation in combination with iontophoresis can be used with improved catheters of the present invention to provide improved and extended drug and gene therapy.

A problem with the prior device is that blood may continue to flow and carry away the therapeutic fluid medium before treatment is completed.

Therefore, it is desirable that means be available for confining the therapeutic fluid to the treated area during treatment.

It is also desirable that improved catheters for drug and gene delivery to cells and for electric field generation be available.

It is also desirable that improved methods for drug and gene delivery to cells and for electric field generation for iontophoresis and electroporation be available.

SUMMARY OF THE INVENTION

Accordingly, it is an object of the present invention to provide an improved apparatus and method of electroporation mediated, in vivo, drug and gene delivery into the endothelial and other cells of a patient.

It is another object of the present invention to provide an improved apparatus for combined iontophoresis and electroporation mediated, in vivo, intra cellular drug and gene delivery into the cells of a patient.

According to a primary aspect of the present invention a catheter device is provided with an expandable distal portion carrying circumferentially spaced electrodes for generating electric fields, infusion means for infusion of fluid medium for carrying genes and drugs, and expandable sealing means at each end of the electrodes for sealing off and confining the therapeutic medium to the area to be treated. The catheter is inserted into a selected blood vessel of a patient and advanced to a preselected location within the blood vessel where the endothelial cells on the inner wall of the vessel or cells nearby the blood vessel are to be treated. Once in place, the catheter device is expanded so that the treatment area is first sealed off and then the plurality of spaced electrodes carried thereby are expanded into contact with the inner wall of the blood vessel. A fluid medium is infused into the blood vessel within the sealed area adjacent the electrodes via the catheter and a conventional pump. A power pack connected to the electrodes is energized to apply a predetermined voltage pulse to the electrodes. This subjects the endothelial or other cells to electric fields of predetermined amplitude and duration in order to make the walls of the endothelial cells transiently permeable to permit therapeutic genes or drugs carried by the fluid medium to enter the cells without killing them.

In accordance with another aspect of the invention the fluid medium carrying the genes or drugs serves as one or more of the conductors and pores open to the inside wall of the vessel act as microelectrodes.

In accordance with another aspect of the invention, iontophoresis is used to move the drugs or genes past the endothelial cells to adjacent cells or cells in adjacent tissue for treatment by electroporation.

BRIEF DESCRIPTION OF THE DRAWINGS

Throughout the drawing figures like reference numerals refer to like parts.

DESCRIPTION OF THE PREFERRED EMBODIMENTS

Figure 1:
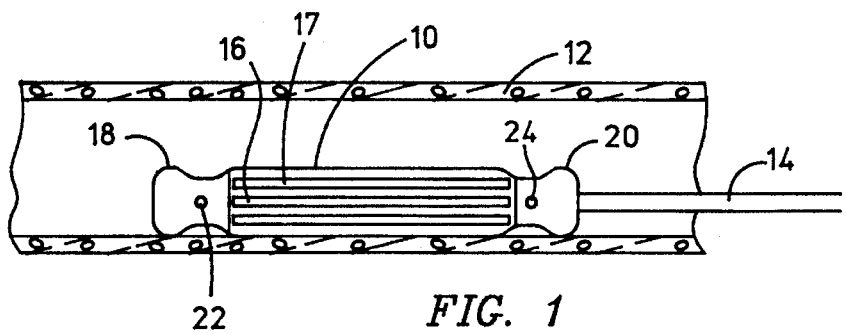
FIG. 1 is a side elevation view illustrating an apparatus in accordance with the present invention implanted in a blood vessel.

Referring to FIG. 1, a first embodiment of our apparatus includes an expandable catheter device 10 in accordance with a preferred embodiment of the invention which is implanted in the blood vessel 12 of a patient which is to receive therapeutic treatment. The device 10 is on a distal end of an elongated catheter or tube 14 which may be used to position the device 10. The device may also be positioned by means of an elongated guide wire. The device includes a plurality of axially extending, circumferentially spaced pairs of electrodes 16 and 17 to which voltage is supplied for repeatedly generating electric fields of a predetermined amplitude and duration. Pairs of the electrodes are preferably spaced a fixed distance apart in order to more precisely control the electrical fields.

Figure 2:
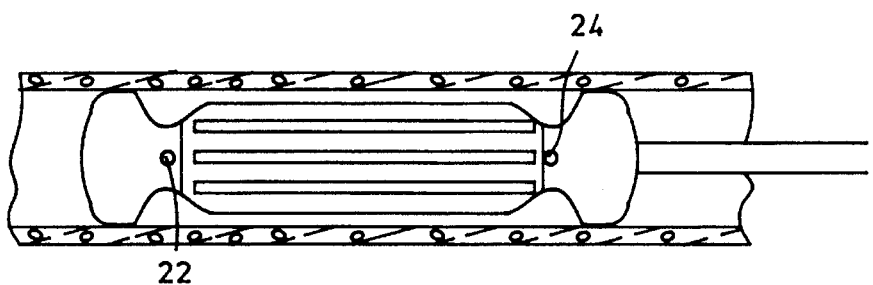
FIG. 2 is a view like FIG. 1 of embodiment of FIG. 1 partially inflated in the blood vessel.
Figure 3:
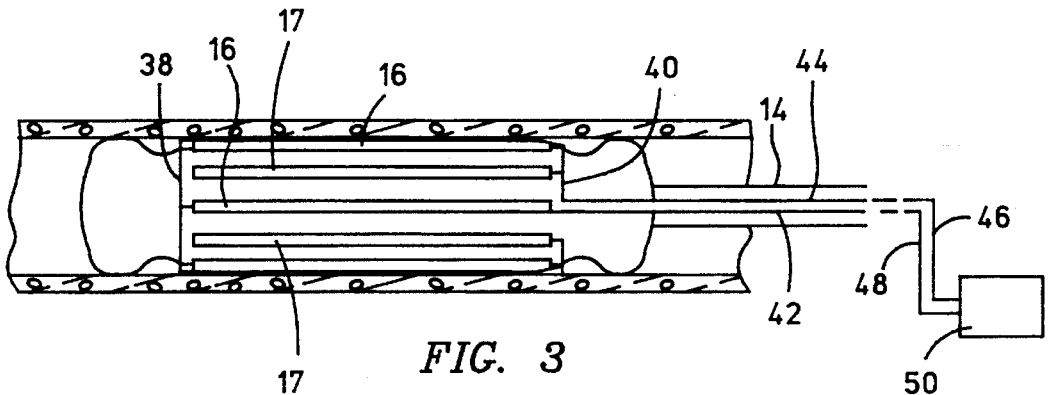
FIG. 3 illustrates the embodiment of FIG. 1 fully inflated in the blood vessel.

The catheter device 10 is expandable to position the electrodes in contact with the inside of the walls of the blood vessels. The device may be expandable in any number of ways such as disclosed in the parent application which is incorporated herein by reference as though fully set forth. However, in the illustrated embodiment the device is in the form of a balloon and is expandable by inflation by means of a gas such as nitrogen or other inert gas or a liquid. The body of the device is formed of an elongated balloon like structure having annular or circumferential seal portions or members 18 and 20 at each-end of the body. These seals expand and engage the vessel walls first as shown in FIG. 2. so that a medium containing macromolecules is confined to the area of the electrodes. The seals may be either slightly larger in diameter than the main body of the device or they may be slightly thinner so that they expand first.

As the balloon is further inflated, the electrodes engage the inner surface of the walls of the blood vessels. The fluid medium may be infused prior to or after full inflation of the balloon for contact of the electrodes with the inner walls. The device is on one end (distal end) of the tube or catheter 14 which is preferably a tube with sufficient stiffness to push along a vessel. The tube is preferably double lumen with one communicating with the interior of the balloon body to carry gas or liquid for inflation. The other lumen communicates with a plurality of circumferentially spaced injection or infusion ports 22 and 24 at opposite ends of the inflatable body. In the illustrated embodiment, the tube 14 is shown as an outer tube which has a passage 26 communicating via a tube 28 with a source of pressurized gas 30 for inflating purposes. The inflation gas may be nitrogen or other suitable inert gas. A tube 32 connects with ports 22 and 24 and extends along tube 14 and connects via a line 34 to a source 36 of fluid medium containing molecules or macromolecules for infusion into the vessel. The source 36 includes a pump or other pressurization means to deliver the fluid medium carrying preselected molecules such as genes or pharmacological compounds for introduction into the blood vessel 12 adjacent the electrodes 16 and 17.

The pairs of electrodes 16 and 17 are spaced apart conductive strips such as thin wires or tape mounted on a supporting nonconductive strip so that they are maintained a predetermined distance apart. The electrodes are connected by conductive circumferential strips 38 and 40 running around the balloon device and conductors 42 and 44 along tube 14. The conductors 42 and 44 are connected by conductors 46 and 48 to an electrical power unit 50 for applying voltage pulses to the electrodes.

The electrodes 16 are connected to common conductor 38 and the electrodes 17 to common conductor 40. The electric fields are generated by applying a predetermined voltage to the electrodes 16 and 17. The parameters of the voltage, amplitude and pulse length are selected so that the inner wall of the selected blood vessel is subjected to short pulses of high intensity electric fields. These fields make the endothelial cells on the inner wall of the blood vessel transiently permeable to permit the macromolecules to enter the endothelial cells without killing them. The permeability results from the temporary formation of pores in the cell walls which are large enough to permit trans-migration of the macromolecules.

Figure 5:
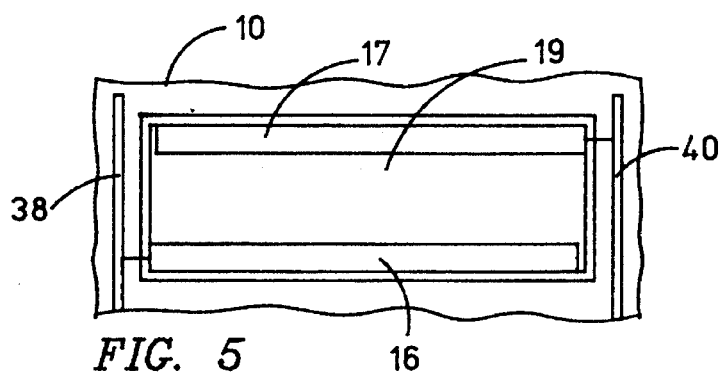
FIG. 5 is an enlarged detail view illustrating details of the electrode mounting.

Each of the electrodes 16 and 17 comprises a metal strip supported in spaced relation on an underlying non-conductive strip 19 as shown in FIG. 5. The non-conductive strips may be made of a plastic material such as that sold under the trademark TEFLON so that the catheter device 10 can be surgically implanted within the surrounding blood vessel 12 with minimal complications from blood clotting. The electrodes 16 and 17 are also preferably coated with a semipermeable layer to impede localized blood clotting. TEFLON material can be made which has pores which are too small to permit blood cells to pass through the same, but the pores are large enough for electrons and ions to carry the electroporation current.

Figure 4:
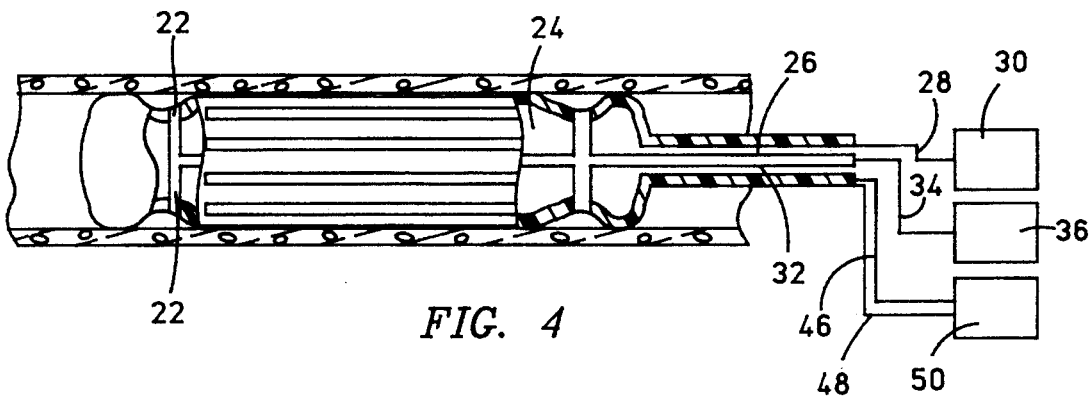
FIG. 4 is a view like FIG. 3 with portions broken away to reveal details.

The electrodes 16 and 17 are connected via wires which extend on or within the tubing 14. These wires or conductors are illustrated diagrammatically at 42 and 44. The wires 42 and 44 are connected via wires 46 and 48 to a power pack 50 outside the patient's body. The power pack is illustrated diagrammatically as a box labeled 50. It supplies the predetermined voltage pulses to the electrodes 16 and 17 which are required to generate the desired electrical fields. A supply pump 36 mounted outside the patient's body supplies the fluid medium carrying the drugs or genes through the injection tubes 32 which carry the medium to injection ports 22 and 24. The supply pump is also illustrated diagrammatically as a box labeled 36 in FIG. 4. It may be of the conventional type that employs a syringe for holding a predetermined quantity of the fluid medium.

The catheter device 10 can be inserted into the selected blood vessel 12 and advanced to a preselected location within the blood vessel where either endothelial cells on the inner wall of the vessel or cells in an adjacent area are to be treated. Once in place, the seals 18 and 20 are expanded to engage the vessel wall first. The fluid medium is then infused into the blood vessel adjacent the electrodes 16 via ports 22 and 24 by pump 36. Then the catheter device is expanded so that the electrodes 16 and 17 are in contact with the inner wall of the blood vessel. The pump 36 may be a typical syringe where the plunger is driven by a motor. The power pack 50 is energized to apply a predetermined voltage pulse to the electrodes 16 and 17 thereby subjecting the endothelial cells to electric fields of predetermined amplitude and duration in order to make the walls of the endothelial cells transiently permeable to permit genes or drugs carried by the fluid medium to enter the endothelial cells without killing them. Where cells inside the blood vessel walls (i.e. adjacent tissue) are to be treated, the molecules are first moved from the blood vessel to the cells to be treated by a process of iontophoresis. A low amplitude electric field is applied to transport the charged molecules along existing pathways into or through tissue to the treatment site. Once the molecules are adjacent to the cells to be treated, a high amplitude electric field is applied for electroporation to enable the molecules to enter the cells.

Where genes are to be infused into the patient, the fluid medium is selected so that it will support the viability of the genes until they are inserted into the blood cells of the patient. Such fluid mediums are well known to those skilled in the art. The plunger of the syringe may be pushed inwardly by a motor driven piston assembly. The rate of delivery of the fluid medium from the syringe through the injection tubes may be manually adjusted via controls with the delivery parameters being indicated on a display.

The function of the power pack 50 is to generate predetermined voltage pulses which, when applied to the electrodes 16, result in applying electric fields of a predetermined amplitude and duration so that the drugs or genes can enter the tissue by iontophoresis and/or enter the endothelial or other cells via electroporation. Preferably, for electroporation, these fields are applied repeatedly and their amplitude and duration make the walls of the endothelial or other cells sufficiently permeable to permit the drugs or genes to enter the endothelial cells without killing them.

One suitable power pack is the ELECTRO CELL MANIPULATOR Model ECM 600 voltage generator commercially available from BTX, Inc. of San Diego, Calif., U.S.A. The ECM 600 voltage generator generates a pulse from the complete discharge of a capacitor which results in an exponentially decaying waveform. The voltage pulse generated by the ECM 600 voltage generator is characterized by a fast rise time and an exponential tail. In the ECM 600 voltage generator, the electroporation pulse length is set by selecting one of ten timing resistors marked R1 through R10. They are active in both High Voltage Mode (HVM) (capacitance fixed at fifty microfarad) and Low Voltage Mode (LVM) (with a capacitance range from 25 to 3,175 microfarad).

The application of an electrical field across the cell membrane results in the creation of transient pores which are critical to the electroporation process. The ECM 600 signal generator provides the voltage (in kV) that travels across the gap (in cm) between the adjacent pairs of electrodes 16 and 17. This potential difference defines what is called the electric field strength where E equals kV/cm. Each cell species has its own critical field strength for optimum electroporation. This is due to cell size, membrane make-up and individual characteristics of the cell wall itself. For example, mammalian cells require typically between 0.5 and 5 kV/cm before cell death and/or electroporation occurs. Generally, the required field strength varies inversely to the size of the cell.

The ECM 600 signal generator has a knob that permits the adjustment of the amplitude of the set charging voltage applied to the internal capacitors from 50 to 500 volts in LVM and from 0.05 to 2.5 kV in the HVM. The maximum amplitude of the voltage pulses is shown on a display incorporated into the ECM 600 signal generator. This device further includes a plurality of push button switches for controlling pulse length, in the LVM, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the catheter device in an automatic cycle that takes less than five seconds. The manual button may be sequentially pressed to repeatedly apply the predetermined voltage pulse to the medium or a repetitive charge/pulse mode may be selected with an adjustable repetition rate. By selecting the electrical parameters of the pulses, the preferred insertion into endothelial cells is possible.

The waveforms of the voltage pulse provided by the generator in the power pack can be an exponentially decaying pulse, a square pulse, a unipolar oscillating pulse train or a bipolar oscillating pulse train. The electric field strength can be 0.2 kV cm to 20 k V/cm. The pulse length can be ten microseconds to one hundred milliseconds. There can be from one up to one hundred pulses applied to an area or a group of cells. Of course, the waveform, electric field strength and pulse duration are dependent upon the exact construction of the catheter device 10 and the type of molecules that are to enter the endothelial cells via electroporation.

Figure 6:
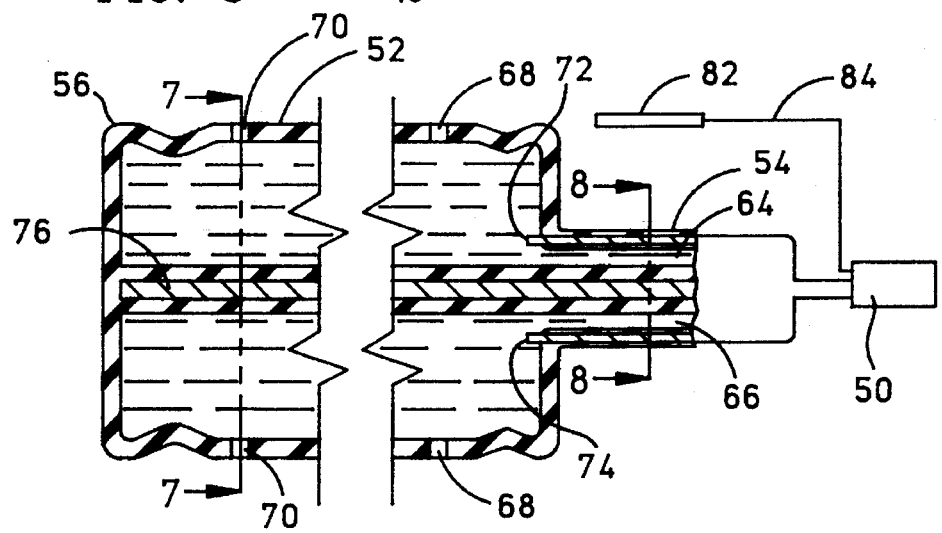
FIG. 6 is an enlarged partial view, in section illustrating details of an alternate embodiment of the invention.
Figure 8:
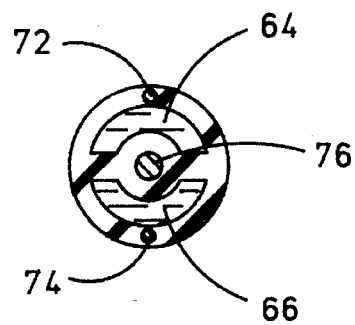
FIG. 8 is a view taken generally on line 8—8 of FIG. 6.
Figure 7:
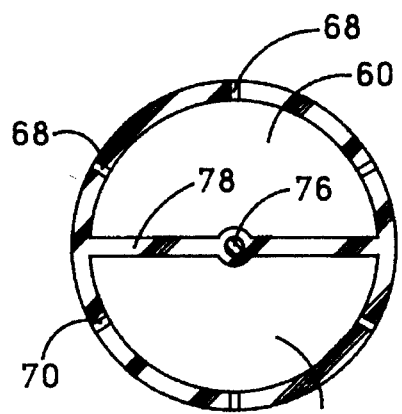
FIG. 7 is a view taken generally on line 7—7 of FIG. 6.

Referring to FIGS. 6 through 8 of the drawings an alternate embodiment of the invention is illustrated wherein an elongated catheter device has a balloon type distal or outer end 52 on the outer or distal end of an elongated catheter member 54. The balloon catheter portion on device 52 is constructed to be expandable or inflatable as in the previously discussed embodiments by means of either a gas or a liquid. The balloon may be inflated by means of a separate chamber as in prior embodiments or by means of the fluid medium carrying the molecules to be infused. The ports 68 and 70 may be sufficiently small that the fluid medium infused applies sufficient pressure to inflate the balloon. As the balloon expands, the ports also expand to infuse the liquid medium and relieve the inflating pressure. The ports may also partially close as the balloon expands into the wall of the blood vessel. It is also preferably provided with seal means 56 and 58 at opposite ends thereof. The balloon device is separated into first and second chambers 60 and 62, each communicating by separate lumen 64 and 66 to a source of fluid medium, such as a liquid carrying either drugs or genes, as previously discussed.

The liquid medium is typically conductive and in the illustrated embodiment will communicate by way of pores 68 from chamber 60 and 70 from chamber 62 with the surface of the blood vessel wall. A pair of electrical conductors 72 and 74 are embedded in the walls of the catheter 54 and connected to the power source for conducting electrical currant to the chambers 60 and 62. This results in the pores 68 and 70 acting as opposed electrodes and thereby inducing an electric field in the walls of the blood vessel, or an adjacent area. In the illustrated embodiment the voltage can be supplied through the medium communicating by a way of the lumens 64 and 66. However, in order to reduce the electrical resistance in the circuit, it is preferable to utilize conductive wires 72 and 74. One or the other of these electrodes may also act with an outside electrode 82 when carrying out iontophoresis.

In a typical embodiment, the catheter may preferably include a central guidewire 76 which may be used to guide and force the catheter along the blood vessel. The guidewire in the FIG. 7 embodiment may preferably be embodied in a wall 78 forming a partition between the two chambers 60 and 62.

Figure 9:
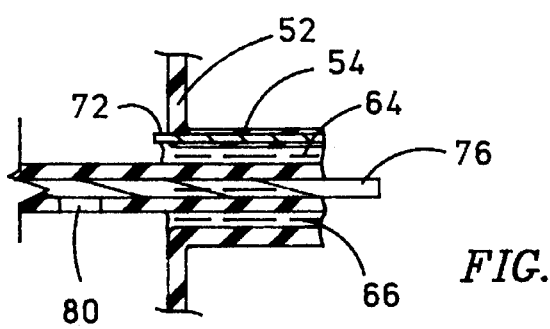
FIG. 9 is a partial view like a portion of FIG. 6 of a further embodiment of the invention.

Referring to FIG. 9, an alternate embodiment is illustrated wherein the guidewire 76 is uncovered and exposed at an area 80 providing a conductive path, so that the guidewire 76 acts as a conductor to the medium in one chamber, such as 62. The other chamber is connected by way of a conductor 72 as in the prior illustrated embodiment.

The apparatus of the present invention is also contemplated to be used in a combined procedure wherein both iontophoresis and electroporation are utilized to transport charged molecules along existing pathways into or through tissue and thereafter apply a electroporation technique. Iontophoresis is a technique utilizing low amplitude electric fields to transport charged molecules along existing pathways into or through tissue to preselected sites. Electroporation is a technique utilizing short, high-amplitude pulses of electric fields to create transit pores in cell membranes so that molecules can enter. A process of the present invention combines both techniques in one catheter to transport molecules first by iontophoresis into the inner walls of vessels and then by electroporation into the interior of the cells. Because of iontophoresis requires very low field strength, a second electrode does not need to be in close proximity of the first electrode, but rather can be outside on the surface of the human body.

Referring to FIG. 6, an electrode 82 is illustrated for positioning outside the body and connected by a conductor 84 to the power source 50. This electrode is used in conjunction with an electrode on the balloon catheter to drive the molecules into or through the blood vessel walls to a selected site.

After driving the molecules into or through the vessel walls by means of iontophoresis, electroporation can be performed generating locally high-intensity pulses of electric fields, for example between sets of pores of the balloon, or between one set of pores in the balloon and an electrode structure on the outside of the balloon, or between two electrode structures on the outside of the balloon. Thus, the method and apparatus of the present invention provides a highly flexible apparatus and technique for gene and drug therapy and treatment.

While we have described preferred embodiments of our catheter device and our method for drug and gene delivery to endothelial cells, it should be understood that modifications and adaptations thereof will occur to persons skilled in the art. Therefore, the protection afforded our invention should only be limited in accordance with the scope of the following claims.

We claim:

1. An in vivo method of introducing molecules into cells of a patient for therapeutic purposes, comprising the steps of:

providing an implantable catheter means including an expandable distal portion having separate seal means at each end thereof and opposed multiple conductor means between the seal means for generating an electric field;

implanting the device at a selected location into a selected blood vessel of the patient for generating an electric field adjacent to an inner wall of the selected blood vessel;

activating the seal means for sealing off the blood vessel on both sides of the selected location;

infusing preselected macromolecules into the selected blood vessel at the selected location; and applying a predetermined electric signal to the implanted device for repeatedly subjecting a plurality of cells at the predetermined location to electric fields of a predetermined amplitude and duration sufficient to make the walls of the cells transiently permeable for enabling the molecules to enter said cells.

2. A method according to claim 1 wherein the molecules are selected from the group consisting of genes and pharmacological compounds.

3. A method according to claim 1 wherein the electric signal is a pulse having a wave form selected from the group consisting of an exponentially decaying pulse, a square pulse, a unipolar oscillating pulse train and a bipolar oscillating pulse train.

4. A method according to claim 3 wherein the electric field has a strength of between approximately 0.2 kV/cm and 20.0 kV/cm.

5. A method according to claim 4 wherein each pulse has a duration of between approximately ten microseconds and one hundred milliseconds.

6. A method according to claim 3 wherein there are between approximately one pulse and one hundred pulses for a given location as the unit passes through the selected blood vessel.

7. A method according to claim 1 wherein a low amplitude electric field is first applied to transport the molecules through the tissue to the cells to be treated.

8. A method according to claim 7 wherein said low amplitude electric field is applied to a first electrode in the device and a second electrode outside the patients body.

9. An in vivo method of introducing molecules into cells of a patient for therapeutic purposes, comprising the steps of:

implanting a catheter having a distal portion with a plurality of axially extending, circumferentially spaced pairs of electrodes into a selected blood vessel of the patient for generating an electric field adjacent to an inner wall of the selected blood vessel at a selected location to be treated;

sealing off the blood vessel on both sides of the selected location;

infusing preselected macromolecules into the selected blood vessel at the selected location; and applying a predetermined electric signal to the implanted device to repeatedly subject a plurality of cells at the predetermined location in electric fields of a predetermined amplitude and duration to make the walls of the cells transiently permeable to permit the molecules to enter said cells.

10. A method according to claim 9 wherein the step of implanting the catheter includes providing a catheter wherein the distal portion is expandable, inserting the distal portion into the selected blood vessel and expanding the distal portion to place the electrodes into contact with the inner surface of the blood vessel.

11. An apparatus for introducing molecules into cells at a selected location via a blood vessel of a patient, comprising:

implantable catheter means having a distal portion and field generating means including multiple electrodes of opposite polarity on said distal portion for generating an electric field at a predetermined location within a selected blood vessel of a patient;

expandable seal means separately disposed at opposite ends of said distal portion for sealing the electrodes within the predetermined location of the blood vessel;

means for expanding the seal means;

infusion ports in said distal portion for infusing a predetermined quantity of a fluid medium carrying preselected molecules into the selected blood vessel at the predetermined location: and means for applying voltage pulses to the field generating means for repeatedly generating electric fields of a predetermined amplitude and duration sufficient for inducing the walls of a plurality of cells at the predetermined location to be transiently permeable to enable the molecules to enter said cells.

12. An apparatus according to claim 11 wherein the field generating means on said distal portion comprises a plurality of axially extending, circumferentially spaced pairs of electrodes, and said seal means are disposed at each end of said electrodes for sealing the quantity of fluid carrying the molecules in the predetermined location.

13. An apparatus according to claim 12 wherein the means for applying voltage pulses to the field generating means includes a voltage generator for generating the voltage pulses.

14. An apparatus according to claim 11 wherein the multiple electrodes includes a plurality of spaced apart pairs of electrodes disposed between said seal means, wherein said distal portion is expandable, and further comprising means for expanding said distal portion for positioning the electrodes against the walls of the blood vessel.

15. An apparatus according to claim 14 wherein the electrodes extend in an axial direction and are circumferentially spaced and wherein the pairs are a predetermined spaced distance apart.

16. An apparatus according to claim 11 wherein the electrodes comprise at least one conductive fluid, and the infusion ports communicate the fluid to the wall of the blood vessel.

17. An apparatus according to claim 16 wherein the field generating means includes an external electrode.

18. An apparatus according to claim 11 wherein the distal portion includes an inflatable balloon between said seal means, a plurality of infusion ports in said balloon between said seal means, and said catheter means includes means for communicating a pressurized fluid for inflating the balloon.

19. An apparatus according to claim 18 wherein the electrodes comprise at least one conductive fluid, and means including said infusion ports communicating the fluid to the wall of the blood vessel.

20. An apparatus according to claim 18 wherein the field generating means includes an exterior electrode.

21. An apparatus according to claim 11 wherein the electrodes include a plurality of spaced apart electrodes disposed between said seal means, and means for expanding the electrodes against the walls of the blood vessel.

22. An apparatus for introducing molecules into cells at a selected location via a blood vessel of a patient, comprising:

implantable catheter means having a distal portion having a plurality of circumferentially spaced pairs of electrodes wherein the pairs are a predetermined spaced distance apart for generating an electric field at a predetermined location within a selected blood vessel of a patient;

seal means for sealing the distal portion within the predetermined location of the blood vessel;

and means for infusing a predetermined quantity of a fluid medium carrying preselected molecules into the selected blood vessel at the predetermined location, wherein the electrodes are supported on a plurality of axially extending non-conductive strips which are circumferentially spaced and the distal portion includes means for expanding the electrodes comprising an inflatable balloon and means for inflating the balloon.

* * * * *